(12) United States Patent
Dai et al.

(10) Patent No.: US 11,530,390 B2
(45) Date of Patent: Dec. 20, 2022

(54) METHOD FOR PROMOTING REPLICATION OF BOVINE RHINOTRACHEITIS VIRUSES USING COLD ATMOSPHERIC PLASMA

(71) Applicant: Wuxi Daixifen Biotechnology Co., Ltd, Jiangsu (CN)

(72) Inventors: Xiaofeng Dai, Jiangsu (CN); Xuanhao Zhang, Jiangsu (CN); Jianying Zhang, Jiangsu (CN)

(73) Assignee: JIANGSU CAPTAIN BIOTECHNOLOGY CO., LTD., Nanjing (CN)

( * ) Notice: Subject to any disclaimer, the term of this patent is extended or adjusted under 35 U.S.C. 154(b) by 916 days.

(21) Appl. No.: 16/388,823

(22) Filed: Apr. 18, 2019

(65) Prior Publication Data

US 2019/0330598 A1    Oct. 31, 2019

(30) Foreign Application Priority Data

Apr. 25, 2018  (CN) .......................... 201810377315.6

(51) Int. Cl.

| | |
|---|---|
| *C12N 7/00* | (2006.01) |
| *A61P 31/22* | (2006.01) |
| *A61K 39/265* | (2006.01) |
| *C12N 5/071* | (2010.01) |
| *A61K 39/00* | (2006.01) |

(52) U.S. Cl.
CPC .............. *C12N 7/00* (2013.01); *A61K 39/265* (2013.01); *A61P 31/22* (2018.01); *C12N 5/0686* (2013.01); *A61K 2039/552* (2013.01); *C12N 2502/25* (2013.01); *C12N 2511/00* (2013.01); *C12N 2710/16721* (2013.01)

(58) Field of Classification Search
None
See application file for complete search history.

(56) References Cited

PUBLICATIONS

Miao et al. Cold atmospheric plasma increases IBRV titer in MDBK cells by orchestrating the host cell network. Virulence, 2021, 12: 1,679-689.*

* cited by examiner

*Primary Examiner* — Nianxiang Zou

(57) ABSTRACT

A method for promoting replication of infectious bovine rhinotracheitis viruses using cold atmospheric plasma, including: irradiating a medium for Madin-Darby bovine kidney cells with a cold atmospheric plasma generator; adding the irradiated medium to the Madin-Darby bovine kidney cells; and adding infectious bovine rhinotracheitis viruses for incubation. The time required for treatment is 2 min allowing for a simple and rapid operation. The plasma is used for the indirect treatment of cells with a uniform process and a controllable intensity. The replication of the infectious bovine rhinotracheitis viruses in the Madin-Darby bovine kidney cells is significantly promoted by co-incubation in the treated DMEM for 1 hour, so that the high levels of infectious bovine rhinotracheitis viruses obtained can be used for vaccine production after inactivation, improving the vaccine production efficiency.

20 Claims, 3 Drawing Sheets

METHOD FOR PROMOTING REPLICATION OF BOVINE RHINOTRACHEITIS VIRUSES USING COLD ATMOSPHERIC PLASMA

CROSS-REFERENCE TO RELATED APPLICATIONS

This application claims the benefit of priority from Chinese Patent Application No. CN 201810377315.6, filed on Apr. 25, 2018. The content of the aforementioned application, including any intervening amendments thereto, is incorporated herein by reference in its entirety.

TECHNICAL FIELD

The present invention relates to vaccine production, and specifically to a method for promoting replication of infectious bovine rhinotracheitis viruses.

BACKGROUND OF THE INVENTION

Infectious bovine rhinotracheitis virus (IBRV) is a virus of the family *herpesviridae* and is double-stranded DNA, which is an major pathogen of infectious diseases in bovines. Infectious bovine rhinotracheitis (IBR) has become a global epidemic, causing significant economic losses in the cattle industry. At present, there is a relatively high IBR prevalence rate in China, and due to the poor therapeutic effect in clinical practice, vaccination is often adopted to prevent IBR.

The conventional vaccines that are commercially available mainly include inactivated vaccines and attenuated vaccines. How to increase vaccine production and reduce the cost of vaccine production has become a key problem in vaccine production. Therefore, there is an urgent need to develop a method for promoting the replication of IBRV to solve the problems in the prior art, thus improving the vaccine production efficiency.

SUMMARY OF THE INVENTION

This section is to illustrate some aspects of the application. Simplifications and omissions may be made in terms of the summary, the abstract and the title to make their purposes clear. These simplifications and omissions are not intended to limit the scope of the application.

Accordingly, the present invention provides a method for promoting the replication of infectious bovine rhinotracheitis viruses (IBRVs) to overcome the defects in the prior art.

A method for promoting the replication of IBRVs includes:

irradiating a medium for Madin-Darby bovine kidney (MDBK) cells with a cold atmospheric plasma generator; adding the irradiated medium to the MDBK cells; and adding IBRVs for incubation.

In an embodiment, the medium includes DMEM.

In an embodiment, in the step of irradiating the DMEM with the cold atmospheric plasma generator, a helium flow rate is controlled to 1 slm and an output voltage of a high-frequency power supply is controlled to 0.96-1.24 kV by a transformer.

In an embodiment, in the step of irradiating the DMEM with the cold atmospheric plasma generator, the DMEM is placed under the cold atmospheric plasma generator; where a distance between an end of the plasma beam and the DMEM is controlled to 1 cm.

In an embodiment, an irradiation time is 2 min.

In an embodiment, the method further includes:

plating the MDBK cells into a 6-well plate with 500,000 cells per well one day before the medium for the MDBK cells is irradiated with the cold atmospheric plasma generator.

In an embodiment, the irradiated medium is added to the MDBK cells with 1 mL medium per well.

In an embodiment, the step of adding IBRV for incubation includes: carrying out the incubation in an incubator at 37° C. for 1 hour after the IBRVs are added.

In an embodiment, the method further includes: culturing the MDBK cells with a 1640 medium containing 2% fetal bovine serum until the cells are completely detached, and then collecting the MDBK cells.

The beneficial effects of the invention are described as follows.

The application employs the plasma to indirectly treat the cells with a uniform process and a controllable intensity. The time required for the treatment is only 2 minutes, leading to a simple and rapid operation. The replication of the IBRVs in the MDBK cells is significantly promoted by co-incubation in the treated DMEM for 1 hour, so that the high levels of IBRVs obtained can be used for vaccine production after inactivation, improving the vaccine production efficiency.

BRIEF DESCRIPTION OF THE DRAWINGS

In order to clearly illustrate the technical solutions of the invention, the drawings to which the embodiments refer will be briefly described below. It is obvious that the drawings are only some embodiments of the invention, and based on these one skilled in the art can obtain other figures without any inventive work.

DETAILED DESCRIPTION OF EMBODIMENTS

The embodiments of the present invention will be further described in detail with reference to the accompanying drawings, from which the object, characteristics and advantages become more apparent and clearer.

In order to make the present invention more understandable, some specific details are illustrated below. The present invention can be implemented in other ways that are not described herein, and similar variations can be made by those skilled in the prior art without departing from the spirit of the present invention. Therefore, the scope of the present invention is not limited to the embodiments below.

The term "embodiment(s)" used herein refers to a particular feature, structure, or characteristic that are included in at least one implementation of the invention. The expression "in an embodiment" described in different places are not necessarily the same embodiment, and are not a separate or alternative embodiment that is mutually exclusive with other embodiments.

EXAMPLE 1

Cell Plating

On the day before the experiment, MDBK cells that overgrew were digested with 0.25% trypsin, centrifuged and resuspended followed by counting. The resuspended cells were plated into a 6-well plate with 500,000 cells per well.

Figure 1:
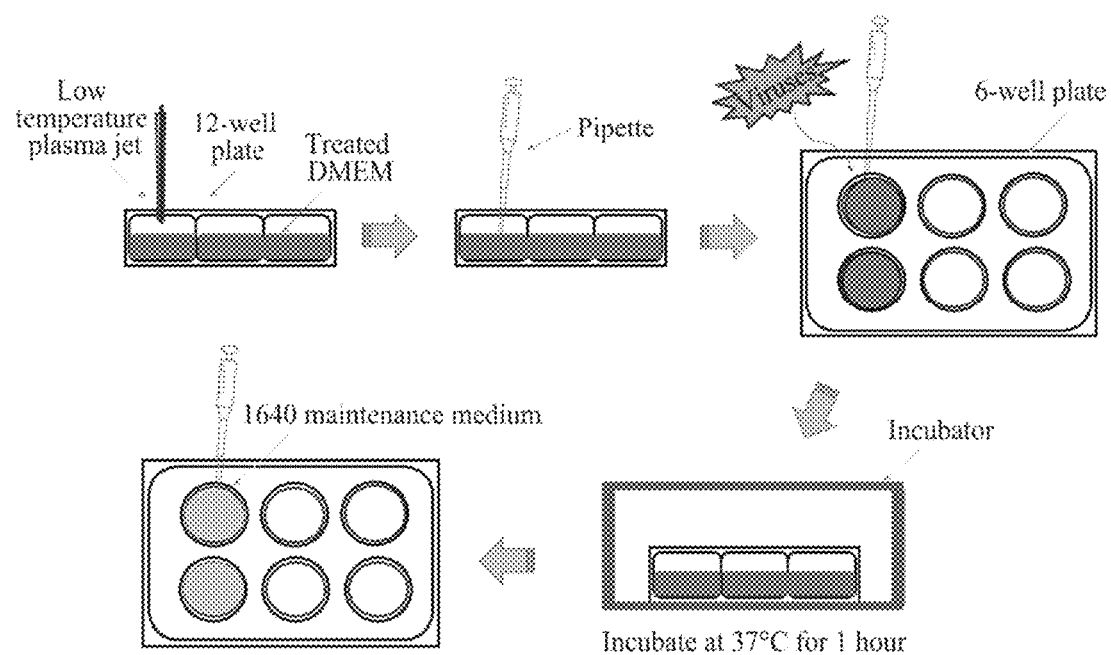
FIG. 1 is a flow chart showing treatment of a medium with a cold atmospheric plasma and incubation of cells according to the present invention.

A blank untreated DMEM was added to a clean 12-well plate with 1 mL of medium per well and placed under a cold atmospheric plasma generator. The distance (D) between the end of the plasma beam and the medium was controlled to 1 cm. The jet orifice was vertically aligned with the center of the wells of the 12-well plate. The helium flow rate (F) was controlled to 1 slm, and the output voltage (U) of the high-frequency power supply was controlled to 0.96-1.24 kV by a transformer. The DMEM was irradiated by the plasma for 2 min. The medium that had been irradiated separately was transferred into a centrifuge tube to which IBRVs were added (2 μL of IBRVs per mL of the medium), and mixed with the medium uniformly. The medium in the 6-well plate was gently pipetted, and the IBRV-containing medium was added to the 6-well plate with 1 mL of medium per well. The untreated IBRV-containing DMEM was used as the control group. After being incubated in an incubator at 37° C. for 1 hour, the 6-well plate was taken out and replaced with a 1640 maintenance medium containing 2% fetal bovine serum (FIG. 1). Then the 6-well plate was continuously cultured in the incubator until the cells were completely detached. The culture media of the control group and the experimental group were collected separately; some were used for the detection of virus amount by fluorescence quantitative PCR (qPCR), and some were used for the determination of virus titer by $TCID_{50}$ assay.

Fluorescence Quantitative PCR (qPCR) Assay

Figure 2:
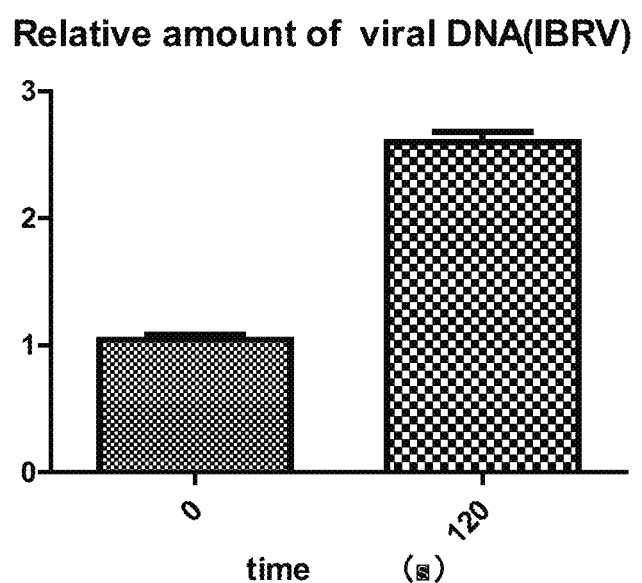
FIG. 2 shows the results of fluorescence quantitative PCR detection for IBRVs, where 0s serves as the control group and 120s means that the treatment time by the cold atmospheric plasma is 2 min.

Genomic DNA of the virus in each culture medium was extracted with a TIANamp Virus DNA/RNA Kit (DP315) (Tiangen Biotech Co., Ltd, Beijing) following its instructions. The extracted genomic DNA was used as a template for fluorescence quantitative PCR to perform a real-time quantitative PCR assay. The fluorescence quantitative PCR detection system was in a volume of 10 μL, which includes: 5 μL of SYBR Green PCR Master Mix, 0.4 μL of upstream primer and 0.4 μL of downstream primer, 2 μL of a boiled supernatant template and 2 μL of ddH$_2$O. The reaction conditions were as follows: pre-denaturation at 95° C. for 30 seconds; 40 cycles with each cycle consisting of 95° C. for 10 seconds, 60° C. for 30 seconds and 72° C. for 20 seconds; melting curve analysis conditions: 95° C. for 15 seconds, 60° C. for 30 seconds and 95° C. for 15 seconds. The results showed that after the IBRVs were co-incubated with MDBK cells in the medium irradiated with the cold atmospheric plasma for 1 hour, the IBRV yield was 2.6-fold higher than the control group through qPCR detection (FIG. 2, where 0s was the control group, and 120s indicated that the treatment time by the cold atmospheric plasma is 2 min).

Virus Titer Determination by $TCID_{50}$ Assay

On the day before the experiment, MDBK cells were digested and plated into a 96-well plate with 10,000 cells per well, which was then incubated at 37° C. for use. According to the determination method, the collected virus culture media of the control group and the experimental group were separately diluted to 6 different dilutions with 1640 medium by a 10-fold serial dilution. Then, the medium in the 96-well plate was pipetted, and viruses of different dilutions in the two groups were added to the wells of the 96-well plate with 8 wells for each dilution. After the 96-well plate was incubated for 1 h, the media were replaced with a maintenance medium. Cytopathic effect (CPE) was observed and recorded every day to calculate the virus titer.

According to the Reed-Muench method, 50% CPE of samples in each of columns was taken as a boundary, and the columns with CPE % next above 50% and next below 50% were used to perform the following calculations:

proportional distance=(percentage of CPE next above 50%−50%)/(percentage of CPE next above 50%−percentage of CPE next below 50%);

LgTCID50=proportional distance×difference between logarithms of dilutions+logarithm of the dilution with CPE next above 50%.

Figure 3:
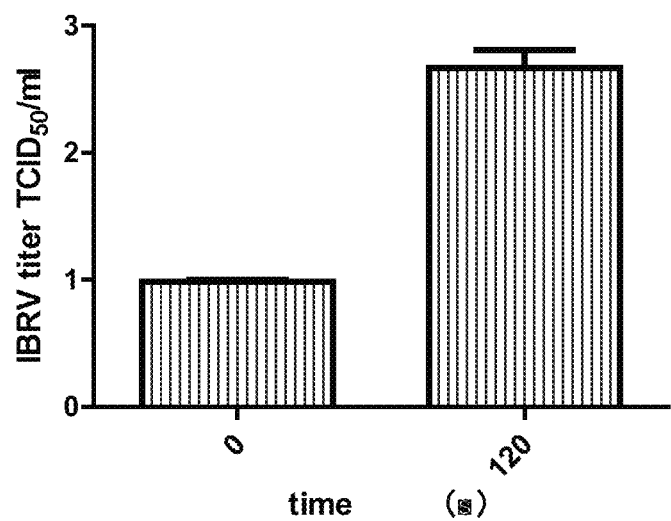
FIG. 3 is a graph showing the results of $TCID_{50}$ assay for IBRVs, where 0s serves as the control group, and 120s means that the treatment time by the cold atmospheric plasma is 2 min.

The results showed that the virus titer measured by TCID50 assay was substantially consistent with the results obtained by qPCR assay. The virus titer of the group treated by the cold atmospheric plasma was 2.19 fold higher than that of the control group (FIG. 3, where 0s was the control group, and 120s indicated that the treatment time by the cold atmospheric plasma is 2 min).

In the present invention, a low temperature plasma generator is employed to generate a plasma beam by ionization of helium so as to treat the medium. During the process, the plasma jet is exposed to air in contact with the medium, and some active substances enter the medium through the plasma jet, producing a large amount of reactive oxygen species and reactive nitrogen species in the medium. Then the viruses are co-incubated with the cells in the treated medium. The results show that such treated medium can promote the replication of IBRVs in the Madin-Darby bovine kidney (MDBK) cells. Compared to the direct treatment of cells by cold atmospheric plasma with potential safety problems, the indirect treatment of the invention is more safe and reliable, and is simple to operate.

The plasma is used for the indirect treatment of cells with a uniform process and a controllable intensity. The replication of the infectious bovine rhinotracheitis viruses in the Madin-Darby bovine kidney cells is significantly promoted by co-incubation in the treated DMEM for 1 hour, so that the high levels of infectious bovine rhinotracheitis viruses obtained can be used for vaccine production after inactivation, improving the vaccine production efficiency.

It should be noted that the above embodiments are merely illustrative of the invention, but are not intended to limit the technical solutions thereof. Although the invention has been described in detail herein with reference to the embodiment, it should be understood by those skilled in the art that modifications or equivalent substitution can be made without departing from the spirit of the invention and should also fall within the scope as defined by the appended claims.

What is claimed is:

1. A method for promoting replication of infectious bovine rhinotracheitis viruses, comprising: irradiating a medium for Madin-Darby bovine kidney (MDBK) cells with a cold atmospheric plasma generator; adding the irradiated medium to the MDBK cells; and adding infectious bovine rhinotracheitis viruses for incubation.

2. The method of claim 1, wherein the medium comprises Dulbecco's modified eagle medium (DMEM).

3. The method of claim 2, wherein in the step of irradiating the DMEM with the cold atmospheric plasma generator, a helium flow rate is controlled to 1 slm and an output voltage of a high-frequency power supply is controlled to 0.96-1.24 kV by a transformer.

4. The method of claim 2, wherein in the step of irradiating the DMEM with the cold atmospheric plasma generator, the DMEM is placed under the cold atmospheric plasma generator; where a distance between an end of the plasma beam and the DMEM is controlled to 1 cm.

5. The method of claim 3, wherein in the step of irradiating the DMEM with the cold atmospheric plasma generator, the DMEM is placed under the cold atmospheric plasma generator; where a distance between an end of the plasma beam and the DMEM is controlled to 1 cm.

6. The method of claim 2, wherein an irradiation time is 2 minutes.

7. The method of claim 3, wherein an irradiation time is 2 minutes.

8. The method of claim 2, further comprising:
plating the MDBK cells to a 6-well plate with 500,000 cells per well one day before the medium for the Madin-Darby bovine kidney cells is irradiated with the cold atmospheric plasma generator.

9. The method of claim 3, further comprising:
plating the MDBK cells to a 6-well plate with 500,000 cells per well one day before the medium for the Madin-Darby bovine kidney cells is irradiated with the cold atmospheric plasma generator.

10. The method of claim 8, wherein the irradiated medium is added to the Madin-Darby bovine kidney cells with 1 mL of irradiated medium per well.

11. The method of claim 9, wherein the irradiated medium is added to the Madin-Darby bovine kidney cells with 1 mL of irradiated medium per well.

12. The method of claim 10, wherein the step of adding infectious bovine rhinotracheitis viruses for incubation comprises: carrying out the incubation in an incubator at 37° C. for 1 hour after the infectious bovine rhinotracheitis viruses are added.

13. The method of claim 11, wherein the step of adding infectious bovine rhinotracheitis viruses for incubation comprises: carrying out the incubation in an incubator at 37° C. for 1 hour after the infectious bovine rhinotracheitis viruses are added.

14. The method of claim 1, further comprising: after the incubation of the infectious bovine rhinotracheitis viruses, culturing the MDBK cells with a 1640 medium containing 2% fetal bovine serum until the cells are completely detached, and then collecting the MDBK cells.

15. The method of claim 2, further comprising: after the incubation of the infectious bovine rhinotracheitis viruses, culturing the MDBK cells with a 1640 medium containing 2% fetal bovine serum until the cells are completely detached, and then collecting the MDBK cells.

16. The method of claim 3, further comprising: after the incubation of the infectious bovine rhinotracheitis viruses, culturing the MDBK cells with a 1640 medium containing 2% fetal bovine serum until the cells are completely detached, and then collecting the MDBK cells.

17. The method of claim 10, further comprising: after the incubation of the infectious bovine rhinotracheitis viruses, culturing the MDBK cells with a 1640 medium containing 2% fetal bovine serum until the cells are completely detached, and then collecting the MDBK cells.

18. The method of claim 11, further comprising: after the incubation of the infectious bovine rhinotracheitis viruses, culturing the MDBK cells with a 1640 medium containing 2% fetal bovine serum until the cells are completely detached, and then collecting the MDBK cells.

19. The method of claim 12, further comprising: after the incubation of the infectious bovine rhinotracheitis viruses, culturing the MDBK cells with a 1640 medium containing 2% fetal bovine serum until the cells are completely detached, and then collecting the MDBK cells.

20. The method of claim 13, further comprising: after the incubation of the infectious bovine rhinotracheitis viruses, culturing the MDBK cells with a 1640 medium containing 2% fetal bovine serum until the cells are completely detached, and then collecting the MDBK cells.

* * * * *